(12) United States Patent
Akhavan et al.

(10) Patent No.: US 6,960,290 B2
(45) Date of Patent: Nov. 1, 2005

(54) TESTING AND CALIBRATION DEVICE FOR AN OXYGEN PROBE EVALUATION CIRCUIT AND METHOD OF USE OF THE DEVICE

(75) Inventors: Dariusch Akhavan, Barbing (DE); Stephan Bolz, Pfatter (DE)

(73) Assignee: Siemens Aktiengesellschaft, Munich (DE)

( * ) Notice: Subject to any disclaimer, the term of this patent is extended or adjusted under 35 U.S.C. 154(b) by 213 days.

(21) Appl. No.: 10/302,065

(22) Filed: Nov. 22, 2002

(65) Prior Publication Data

US 2003/0080003 A1 May 1, 2003

Related U.S. Application Data

(63) Continuation of application No. PCT/DE01/01974, filed on May 22, 2001.

(30) Foreign Application Priority Data

May 24, 2000 (DE) .......................................... 100 25 578

(51) Int. Cl.$^7$ .............................................. G01N 27/41
(52) U.S. Cl. ....................... 205/783; 204/401; 204/424; 73/1.06
(58) Field of Search ................................ 204/401, 406, 204/424, 425; 205/783; 73/23.31, 23.22, 1.06, 1.07; 123/693

(56) References Cited

U.S. PATENT DOCUMENTS

| 4,532,013 | A | | 7/1985 | Dietz et al. |
|---|---|---|---|---|
| 5,298,865 | A | | 3/1994 | Denz et al. |
| 5,448,178 | A | * | 9/1995 | Chen et al. ............... 205/775.5 |
| 5,522,250 | A | * | 6/1996 | Gee et al. ..................... 73/1.07 |
| 5,781,024 | A | * | 7/1998 | Blomberg et al. .......... 324/763 |
| 5,873,990 | A | * | 2/1999 | Wojciechowski et al. ... 204/406 |
| 6,230,543 | B1 | * | 5/2001 | Froehling et al. ............ 73/1.06 |

FOREIGN PATENT DOCUMENTS

| DE | 3840148 A1 | 11/1988 |
|---|---|---|
| DE | 198 36 127 A1 | 8/1998 |
| DE | 198 44 994 A1 | 9/1998 |
| EP | 1 001 261 A1 | 11/1999 |

* cited by examiner

*Primary Examiner*—Kaj K. Olsen
(74) *Attorney, Agent, or Firm*—Baker Botts L.L.P.

(57) ABSTRACT

A testing and calibrating device for an evaluation circuit of a linear oxygen probe (S) of an internal combustion engine is disclosed. Said device comprises a probe equivalent circuit (SES) having the same terminals (Vs+, Vs−/Vp−, Vp+ and Rc) as the oxygen probe (S). The probe equivalent circuit can largely emulate the electrical and chemical behaviors of the oxygen probe (S) and simulate probe faults and, at least during a testing and calibrating process, is connected to the evaluation circuit in place of the oxygen probe (S) or is connected parallel to said oxygen probe.

14 Claims, 1 Drawing Sheet

TESTING AND CALIBRATION DEVICE FOR AN OXYGEN PROBE EVALUATION CIRCUIT AND METHOD OF USE OF THE DEVICE

CROSS REFERENCE TO RELATED APPLICATION

This application is a continuation of copending International Application No. PCT/DE01/01974 filed May 22, 2001, which designates the United States, and claims priority to German application number 10025578.7 filed May 24, 2000.

BACKGROUND OF THE INVENTION

The invention relates to a testing and calibrating device for an evaluation circuit for a linear oxygen probe (referred to below as lambda probe or probe) in an internal combustion engine, particularly in a motor vehicle internal combustion engine.

The production process for engine control circuits for internal combustion engines requires that the probe evaluation circuit be tested and calibrated in the fitted state. This requires that all relevant parameters be verified under operating conditions—various supply voltages and temperatures for the engine control circuit, but also various operating states (lambda values) for the probe. It is also necessary to test whether the evaluation circuit identifies particular probe faults.

Furthermore, it is desirable to be able to perform not only the legally required OBD (on board diagnostics) for the probe but also calibration of the system (probe and evaluation circuit) when the internal combustion engine is operating.

The probe and the evaluation circuit are a closed control system. Simple measurement of the electrical properties of the evaluation circuit (for example offset or gain) is therefore not very revealing. The test needs to be performed when the control loop is closed and stable.

Although a test using a connected lambda probe allows measurement in the operating state, it is time-consuming and imprecise. The addition of a fault to demonstrate the diagnostic function is done using switches in the probe supply lines, for example, which allows short circuits and interruptions to be simulated. This is very time-consuming and susceptible to error. In addition, various operating points of the probe can be measured only by altering the oxygen concentration around the probe. This requires a very complex gas-changing device which regularly needs to be calibrated. Since a gas change, for technical reasons, proceeds comparatively slowly, it is not possible to assess the control stability of the system.

The system (probe and evaluation circuit) is calibrated during engine operation at two operating points:

a) when $\lambda=1$. In this case, no or only a minimal pump current should flow, since the oxygen concentrations in the exhaust from the internal combustion engine and in the measuring cell are balanced;

b) when $\lambda=\infty$, that is to say with no fuel, i.e. when a motor vehicle is in overrun mode. In this case, the (maximum) pump current required is measured.

The values obtained for these two measurements can be used to determine the offset and gradient of the transfer function. The arithmetic values are stored in a correction table.

Overall, the method is extremely complex and has only limited reliability (on account of possible residual exhaust or cooling of the probe in overrun mode).

SUMMARY OF THE INVENTION

It is an object of the invention to provide a testing and calibrating device for an evaluation circuit for a linear lambda probe in an internal combustion engine which provides a simple way of testing and calibrating the evaluation circuit and of adding various faults to demonstrate the diagnostic function during engine operation at prescribed operating points.

The invention achieves this object by a testing and calibrating device for an evaluation circuit for a linear oxygen probe in an internal combustion engine, comprising a probe equivalent circuit having the same connections as the oxygen probe, which largely emulates the electrical and chemical behaviour of the oxygen probe and can simulate probe faults, and which is connected to the evaluation circuit instead of the oxygen probe, or in parallel with it, at least during a testing and calibrating process.

The probe equivalent circuit may comprise an inverting integrator with integral-proportional-integral response, whose non-inverting input is connected to the connection and is connected to the connection via a series circuit comprising a resistor and a resistor, whose inverting input is connected firstly via a resistor to the junction point between the two resistors and to the connection, and secondly via a resistor to a further connection, whose output is connected to its inverting input via a capacitor which has a series circuit comprising a capacitor and a resistor connected in parallel with it, and wherein the inverting integrator has an inverter connected downstream of it, whose inverting input is connected to the output of the integrator via a resistor, whose non-inverting input is connected to the connection, and whose output is connected to its inverting input via a resistor and to the connection via a resistor. A switch can be arranged between the output of the inverter and the resistors, wherein selected potentials can be applied to the connection, for example via an external switch. Furthermore, a switch can be arranged between the output of the integrator and the capacitor, on the one hand, and the resistor on the other. Moreover, a switch can be arranged between the first probe connection and the second probe connection. An external computer may be provided which controls the testing and calibration processes and checks the response of the evaluation circuit under the various operating conditions at the end of production of the evaluation circuit (automated test system). During operation of the oxygen probe, the probe equivalent circuit can be connected in parallel with the oxygen probe at a probe temperature of below 200° C. during the probe's heating phase. The measurement accuracy can be checked and age-related tolerance discrepancies in the evaluation circuit can be equalised by using the probe equivalent circuit in the heating phase of the oxygen probe to set various operating points and by storing the evaluation circuit's pump-current measured values Ip measured in the process for the purpose of further processing.

A method for operating a testing and calibrating device for an evaluation circuit for a linear oxygen probe in an internal combustion engine, comprises the step of:

coupling a probe equivalent circuit having the same connections as the oxygen probe, which largely emulates the electrical and chemical behaviour of the oxygen probe and can simulate probe faults, with the evaluation circuit instead of the oxygen probe during a testing and calibrating process.

The method can further comprise the step of applying selected potentials to the connection, for example, via an external switch. The method can further comprise the step of providing an external computer which controls the testing and calibration processes and checks the response of the evaluation circuit under the various operating conditions at the end of production of the evaluation circuit. During operation of the oxygen probe, the probe equivalent circuit can be connected in parallel with the oxygen probe at a probe temperature of below 200° C. during the probe's heating phase. The measurement accuracy may be checked and age-related tolerance discrepancies in the evaluation circuit can be equalised by using the probe equivalent circuit in the heating phase of the oxygen probe to set various operating points and by storing the evaluation circuit's pump-current measured values Ip measured in the process for the purpose of further processing.

Another method for operating a testing and calibrating device for an evaluation circuit for a linear oxygen probe in an internal combustion engine, comprises the step of:

coupling a probe equivalent circuit having the same connections as the oxygen probe, which largely emulates the electrical and chemical behaviour of the oxygen probe and can simulate probe faults, with the evaluation circuit instead of the oxygen probe in parallel with the oxygen probe, at least during a testing and calibrating process.

The method can further comprise the step of applying selected potentials to the connection, for example, via an external switch. The method can further comprise the step of providing an external computer which controls the testing and calibration processes and checks the response of the evaluation circuit under the various operating conditions at the end of production of the evaluation circuit. The measurement accuracy can be checked and age-related tolerance discrepancies in the evaluation circuit may be equalised by using the probe equivalent circuit in the heating phase of the oxygen probe to set various operating points and by storing the evaluation circuit's pump-current measured values Ip measured in the process for the purpose of further processing.

BRIEF DESCRIPTION OF THE DRAWINGS

The invention is explained in more detail below with reference to a schematic drawing, in which.

DETAILED DESCRIPTION OF THE PREFERRED EMBODIMENTS

Figure 1:
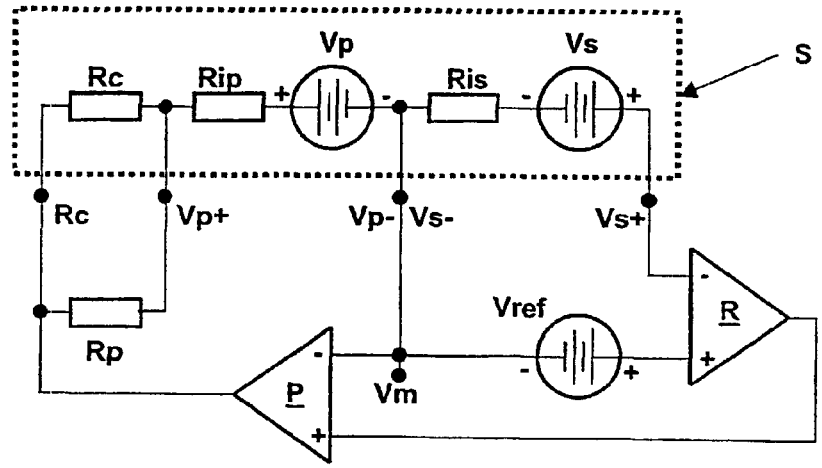
FIG. 1 shows a known, electrical circuit diagram of a lambda probe having an evaluation circuit.

FIG. 1 shows a known, electrical circuit diagram of a lambda probe S (in a dotted frame) having an evaluation circuit for operating a linear lambda probe in an internal combustion engine.

The lambda probe S comprises a) the "reference cell", i.e. the electrodes between measuring chamber and air, shown in the drawing by the Nernst voltage Vs which can be measured between the electrodes and the internal resistance Ris of the diffusion barriers between them, b) the "pump cell", i.e. the electrodes between measuring chamber and exhaust, shown by the voltage Vp drop between them and the (reference) resistance Rip between these electrodes, and c) the calibration resistor Rc in the probe connector.

The electrodes are fitted to the ceramic body of the probe. The ceramic material between the electrode pairs is conductive at high temperatures and serves as a solid electrolyte.

Since the resistor Rc is exposed to considerable environmental stresses on account of its installation position in the probe connector, a further resistor Rp is connected in parallel with it in the control unit. This reduces the influence of Rc on the overall accuracy. Four connections Vs+, Vp−/Vs−, Vp+ and Rc emerge from the probe S and are connected to the evaluation circuit.

The inverting input R− of a differential amplifier or controller R is connected to the connection Vs+ of the probe S, and its non-inverting input R+ is connected to the mid-voltage (Vm) via a reference voltage Vref, where Vm=Vcc/2 and Vcc (normally 5 V) is the supply voltage of the circuit.

The mid-voltage Vm also has the inverting input P− of a pump current source P connected to it, the non-inverting input P+ of said pump current source being connected to the output of the differential amplifier R.

The output of the pump current source P is connected to the input Rc of the probe S.

The differential amplifier/controller R compares the Nernst voltage Vs of the probe S (between external air and measuring cell) with the reference voltage Vref (450 mV) and generates an output voltage which is proportional to the difference and is converted by the pump current source P into a proportional pump current Ip which flows through the pump cell (Rip and Vp) to Vm. The pump current Ip results in a change in the oxygen concentration in the probe's measuring cell (not shown), which in turn results in a change in the Nernst voltage Vs.

The oxygen concentration in the exhaust (lambda) is ascertained by measuring the pump current. To this end, the voltage drop brought about by the pump current Ip across the parallel circuit comprising Rc and Rp is measured using a differential amplifier (not shown).

In a stable control state, the Nernst voltage is Vs=Vref=450 mV: there is a state of equilibrium between the oxygen flow through the diffusion barrier and the oxygen-ion flow, caused by the pump current Ip.

Figure 2:
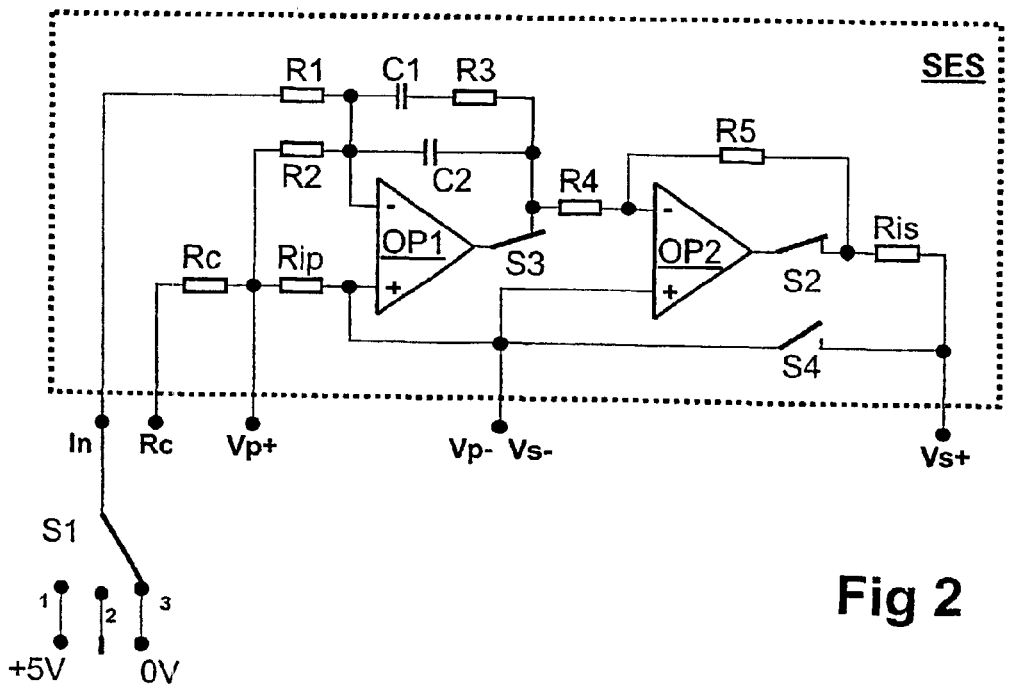
FIG. 2 shows an electrical circuit diagram of a probe equivalent circuit in accordance with the invention.

In line with the invention, during the testing and calibration operation of the evaluation circuit, the lambda probe is replaced by an electronic probe equivalent circuit SES whose electrical circuit diagram is shown in FIG. 2, in a dotted frame.

This probe equivalent circuit SES has the same connections Vs+, Vp−/Vs−, Vp+ and Rc as the lambda probe S shown in FIG. 1 and largely emulates the electrical and chemical behavior thereof.

If the connections of the probe equivalent circuit SES are connected to the corresponding connections of the evaluation circuit, the control loop is closed and a stable operating state (normal state) of the evaluation circuit normally becomes established.

The probe equivalent circuit SES has an inverting integrator with IPI response (Integral-Proportional-Integral response) which is constructed from an operational amplifier OP1, resistors R2 and R3 and capacitors C1 and C2. This integrator emulates the transfer function of the probe in a relevant frequency range.

From the connection Rc, a series circuit comprising a resistor Rc and a resistor Rip is connected to the non-inverting input OP1+ of the operational amplifier OP1. A further resistor R2 is connected between the junction point between the two resistors Rc, Rip and the inverting input OP1− of the operational amplifier OP1. The output of OP1 is connected to a—normally-on—switch S3. Connected between the inverting input OP1− and the other connection of the switch S3 is a capacitor C2 which has a series circuit comprising a capacitor C1 and a resistor R3 connected in parallel with it. The junction point between the two resistors Rc and Rip is connected to the connection Vp+.

The inverting integrator OP1 is followed by an inverter constructed from an operational amplifier OP2 and resistors R4 and R5. It produces the correct phase for the transfer function.

The resistor R4 connects the inverting input OP2− of the operational amplifier OP2 to the output of the operational amplifier OP1. The output of the operational amplifier OP2 is fed back to its inverting input via a—normally-on— switch S2 and the resistor R5. The non-inverting inputs of the two operational amplifiers OP1 and OP2 are connected to one another and to the connection Vp−/Vs−. Connected between the connections Vp−/Vs− and Vs+ is a further— normally-off—switch S4.

The output of the operational amplifier OP2 is connected to the connection Vs+ via the switch S2 and the resistor Ris. The inverting input OP1− of the operational amplifier OP1 is connected via a resistor RI and a further connection In to an external changeover switch S1 which can be used to apply selected potentials to the resistor R1.

The probe equivalent circuit SES can thus be inexpensively produced from standard components.

If the probe equivalent circuit SES shown in FIG. 2 is connected to the evaluation circuit shown in FIG. 1 instead of the probe S, then a closed control loop is obtained. The integrator OP1 will change its output voltage such that its input voltage becomes zero.

If switch S1 is changed to its center position 2, then resistor R1 has no current and the voltage on the inverting input OP1− corresponds to the mid-voltage Vm, for example 2.5 V. Accordingly, the voltage on the non-inverting input OP1+ will also become Vm. No pump current Ip flows and the circuit sets itself to the value $\lambda=1$.

If switch S1 is set to the position 1=0 V (ground), then a voltage divider comprising the resistors R1 and R2 is obtained: the voltage on the inverting input OP1− falls and the inverting integrator OP1 readjusts the pump current Ip via the evaluation circuit. The voltage drop across the resistor Rip causes the voltage on the connection Vp+ to rise Equilibrium has been reached again when the voltage drop across the resistor Rip corresponds to that across resistor R2, and the inverting input OP1− has reached the voltage Vm again.

With appropriate proportioning of the resistors R1 and R2, an operating point $\lambda=\infty$ (air) can thus be set.

If switch S1 is set to position 3=+5 V, then the voltage on the inverting input OP1− will rise, and the inverting integrator OP1 readjusts the pump current Ip via the evaluation circuit, but this time in the other direction. The voltage drop across the resistor Rip causes the voltage on the connection Vp+ to fall. Equilibrium has been reached again when the voltage drop across the resistor Rip corresponds to that across resistor R2, and the inverting input OP1− has reached the voltage Vm again.

With appropriate proportioning of the resistors R1 and R2 (which proportioning can be different than in the case of switch position 1, but does not have to be), an operating point can thus be set which corresponds to a mixed value of, by way of example, $\lambda=0.6$ (rich).

In this way, any operating points from $\lambda=0.6$ (rich) through $\lambda=1$ to $\lambda=\infty$ (air) can be set.

When an AC voltage signal is applied to the input In, it is even possible to ascertain the dynamic response of the control loop comprising evaluation circuit and probe equivalent circuit SES, which has not been possible to date.

Various probe faults can be simulated by operating the (CMOS) switches S2, S3 and S4. In this case, the turning-off of switch S2 corresponds to a faulty (ineffective) pump cell, the turning-off of switch S3 corresponds to an interruption in the measuring cell or in its supply line, and the turning-on of switch S4 corresponds to a short circuit between the probe connections Vp−/Vs− and Vs+. Other faults can be simulated in a similar manner by adding and operating further switches.

In each of these cases, the probe equivalent circuit SES will assume an impermissible operating point which then needs to be identified by a diagnostic circuit (not shown) monitoring the evaluation circuit. This provides a simple way of checking the evaluation circuit's diagnostic function completely.

During production, the probe equivalent circuit SES is controlled by a computer which simultaneously measures the response of the evaluation circuit under various operating conditions (automated test system).

A linear lambda probe has a very high impedance at low temperatures (<200° C.). At the start of the heating phase, the probe is virtually non-existent. It is thus possible to connect the probe equivalent circuit SES to the evaluation circuit in parallel with the probe at this time. The control loop then becomes stabilised via the probe equivalent circuit, so that it is possible to check and calibrate the evaluation circuit during operation. If various operating points are now set (for example $\lambda=0.6$, 1, $\infty$) and the evaluation circuit's associated measured values are stored, it is possible to check the measurement accuracy and to equalise age-related tolerance discrepancies. In this case, the probe equivalent circuit SES can be a fixed (integrated) part of the evaluation circuit. To this end, it merely needs to be isolated from the evaluation circuit by means of (CMOS) switches during normal operation with the real probe.

What is claimed is:

1. A testing and calibrating device for an evaluation circuit for a linear oxygen probe in an internal combustion engine, said device comprising:
   a probe equivalent circuit electrically coupled to the evaluation circuit in the same manner as the oxygen probe is coupled to the evaluation circuit, said probe equivalent circuit configured to emulate the oxygen probe and to simulate probe faults, wherein the probe equivalent circuit is in electical communication with the evaluation circuit instead of the oxygen probe, or in parallel with it, during testing calibration.

2. The device as claimed in claim 1, wherein the probe equivalent circuit comprises an inverting integrator with integral-proportional-integral response,
   wherein the inverting integrator has an inverter connected to.

3. The device as claimed in claim 2, wherein a switch is arranged between an output of the inverter and resistors.

4. The device as claimed in claim 2, wherein a switch is arranged between the output of the integrator
   and a capacitor, and a resistor.

5. The device as claimed in claim 1, wherein an external computer is provided which controls the testing and calibration and checks response of the evaluation circuit under the various operating conditions at the end of production of the evaluation circuit.

6. The device as claimed in claim 1, wherein during operation of the oxygen probe, the probe equivalent circuit is connected in parallel with the oxygen probe at a probe temperature of below 200° C. during a heating phase of the oxygen probe.

7. The device as claimed in claim 6, wherein measurement accuracy is checked and age-related tolerance discrepancies in the evaluation circuit are equalized by using the probe equivalent circuit in the heating phase of the oxygen probe to set various operating points and by storing pump-current measured values Ip of the evaluation circuit.

8. A method for operating a testing and calibrating device for an evaluation circuit for a linear oxygen probe in an internal combustion engine, said method comprising the steps of:

coupling a probe equivalent circuit to the evaluation circuit in the same manner as the oxygen probe is coupled to the evaluation circuit, said probe equivalent circuit configured to emulate, the oxygen probe and to simulate probe faults, wherein said probe equivalent circuit is in electrical communication with the evaluation circuit instead of the oxygen probe during testing and/or calibration.

9. The method as claimed in claim 8, wherein an external computer is provided which controls the testing and calibration and checks response of the evaluation circuit under the various operating conditions at the end of production of the evaluation circuit.

10. The method as claimed in claim 8, wherein during operation of the oxygen probe, the probe equivalent circuit is connected in parallel with the oxygen probe at a probe temperature of below 200° C. during a heating phase of the oxygen probe.

11. The method as claimed in claim 10, wherein measurement accuracy is checked and age-related tolerance discrepancies in the evaluation circuit are equalized by using the probe equivalent circuit in the heating phase of the oxygen probe to set various operating points and by storing pump-current measured values Ip of the evaluation circuit.

12. A method for operating a testing and calibrating device for an evaluation circuit for a linear oxygen probe in an internal combustion engine, said method comprising the steps of:

coupling a probe equivalent circuit to the evaluation circuit in the same manner as the oxygen probe is coupled to the evaluation circuit, said probe equivalent circuit configured to emulate the oxygen probe and to simulate probe faults, wherein the probe equivalent circuit is in electrical communication with the evaluation circuit instead of the oxygen probe and is coupled in parallel with the oxygen probe, during testing and/or calibration.

13. The method as claimed in claim 12, wherein an external computer is provided which controls the testing and calibration and checks response of the evaluation circuit under the various operating conditions at the end of production of the evaluation circuit.

14. The method as claimed in claim 12, wherein measurement accuracy is checked and age-related tolerance discrepancies in the evaluation circuit are equalised by using the probe equivalent circuit in a heating phase of the oxygen probe to set various operating points and by storing the pump-current measured values Ip of the evaluation circuit.

* * * * *